(12) United States Patent
Ichikawa et al.

(10) Patent No.: US 7,577,532 B2
(45) Date of Patent: Aug. 18, 2009

(54) TIRE WEAR DETECTION SYSTEM AND PNEUMATIC TIRE

(75) Inventors: Hiromitsu Ichikawa, Kodaira (JP);
Hiromasa Hada, Kodaira (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 11/630,317

(22) PCT Filed: Jun. 20, 2005

(86) PCT No.: PCT/JP2005/011279

§ 371 (c)(1),
(2), (4) Date: Dec. 21, 2006

(87) PCT Pub. No.: WO2006/001255

PCT Pub. Date: Jan. 5, 2006

(65) Prior Publication Data

US 2008/0027658 A1 Jan. 31, 2008

(30) Foreign Application Priority Data

Jun. 23, 2004 (JP) .............................. 2004-185496

(51) Int. Cl.
*G31B 3/00* (2006.01)
(52) U.S. Cl. ....................................................... 702/34
(58) Field of Classification Search .................... 702/34, 702/41, 47, 96, 98, 104, 116, 138, 141, 148, 702/167, 193; 701/80, 29, 180; 73/146; 340/438, 442
See application file for complete search history.

(56) References Cited

U.S. PATENT DOCUMENTS

| | | | | |
|---|---|---|---|---|
| 5,864,056 A | * | 1/1999 | Bell et al. | ...................... 73/146 |
| 6,076,035 A | * | 6/2000 | Yanase | ......................... 701/80 |
| 6,591,668 B1 | * | 7/2003 | Becherer et al. | .............. 73/146 |
| 6,741,169 B2 | * | 5/2004 | Magiawala et al. | ......... 340/438 |
| 7,203,579 B2 | * | 4/2007 | Yokota et al. | .................. 701/29 |
| 7,391,306 B2 | * | 6/2008 | Dufournier | ................. 340/442 |
| 2002/0121132 A1 | | 9/2002 | Breed et al. | |

FOREIGN PATENT DOCUMENTS

| | | |
|---|---|---|
| DE | 3937966 | 5/1991 |
| DE | 19838638 | 3/2000 |
| JP | 50-94942 A | 7/1975 |
| JP | 56-120901 A | 2/1980 |
| JP | 62-83704 U | 5/1987 |
| JP | 9-193621 A | 7/1997 |
| JP | 11-17-891 A | 6/1999 |
| JP | 2001-215175 A | 8/2001 |
| JP | 2002-104158 A | 4/2002 |
| JP | 2005-178452 A | 7/2005 |
| WO | 0189896 | 11/2001 |

* cited by examiner

*Primary Examiner*—Edward Raymond
*Assistant Examiner*—Mohamed Charioui
(74) *Attorney, Agent, or Firm*—Sughrue Mion, PLLC

(57) ABSTRACT

A tire wear detection system includes a detection unit (70) which detects acceleration applied to a wear bar (40) arranged in a groove of a tread section of a pneumatic tire (10), and a wear judgment unit (82) which judges that a tire has been worn based on the acceleration detected by the detection unit (70).

7 Claims, 4 Drawing Sheets

(a)

(b)

(a)

(b)

TIRE WEAR DETECTION SYSTEM AND PNEUMATIC TIRE

TECHNICAL FIELD

The present invention relates to a tire wear detection system for detecting a worn state of a tire, and a pneumatic tire.

BACKGROUND ART

Conventionally, when a groove of a tire surface is excessively abraded, not only a legal problem has occurred but also running safety has greatly been affected. When managing such tire wear, a driver or a running manager visually checks a groove depth of a tread pattern or an appearance of a wear bar attached to the tire to inspect a worn state of the tire, and replaces the tire with a new tire when the tread has reached a worn state.

To bring this wear bar into clear view, a technology of coloring the wear bar or burying studs to generate abnormal noises has been disclosed (e.g., publication of unexamined utility model application No. 56-120901).

In the case of visually checking the worn state of the tire, when the driver or the like neglects inspection or takes a wrong checking method, it is not preferable because the tire is left as it is even if it reaches its wear limit. Thus, a technology has been disclosed, which detects tire wear by burying an optical reflection member having an optical reflection surface in a tread, the optical reflection surface reflecting a light applied from the outside when the tire is worn, and receiving the light (e.g., publication of unexamined application No. 11-170819).

However, according to the conventional technology described in the Patent Document 1, a tire appearance is damaged and, if anything, because of the buried studs, there is the danger that a road surface will be damaged when the tire is worn, or a damage of the tire will be quickened.

According to the conventional technology described in the Patent Document 2, as the reflected light is detected to check a worn level, when the reflection surface or the light reception surface is stained, the reflected light is not detected even if the reflection surface is exposed. Thus, it may not be recognized even when the tire reaches its wear limit.

Therefore, with the aforementioned problems in mind, it is an object of the present invention to provide a highly reliable tire wear detection system capable of detecting tire wear without damaging a tire or a road surface, and a pneumatic tire.

DISCLOSURE OF THE INVENTION

A first feature of the present invention is a tire wear detection system, including a detection unit which detects acceleration applied to a wear bar arranged in a groove of a tread section of a pneumatic tire, and a wear judgment unit which judges that a tire has been worn based on the acceleration detected by the detection unit.

According to the tire wear detection system of the first feature, the acceleration applied to the wear bar is detected, and thus highly reliable wear detection can be carried out. As a tire surface is not processed, the tire or a road surface is not damaged. Further, as the wear bar arranged in the tire is normally used, it is not necessary to execute any new processing in the tread section.

A second feature of the present invention is a tire wear detection system, including a detection unit which detects a physical amount equivalent to contact of a wear bar arranged in a groove of a tread section of a pneumatic tire with a road surface, and a wear judgment unit which judges that a tire has been worn based on a size of the physical amount.

A third feature of the present invention is a pneumatic tire, including a detection unit which detects acceleration applied to a wear bar arranged in a groove of a tread section of the pneumatic tire.

A fourth feature of the present invention is a pneumatic tire, including a detection unit which detects a physical amount equivalent to contact of a wear bar arranged in a groove of a tread section of the pneumatic tire with a road surface.

BEST MODE OF CARRYING OUT THE INVENTION

Next, the present invention will be described in detail.

(Pneumatic Tire)

First, a pneumatic tire according to an embodiment of the present invention will be described by referring to FIGS. 1 to 2.

Figure 1:
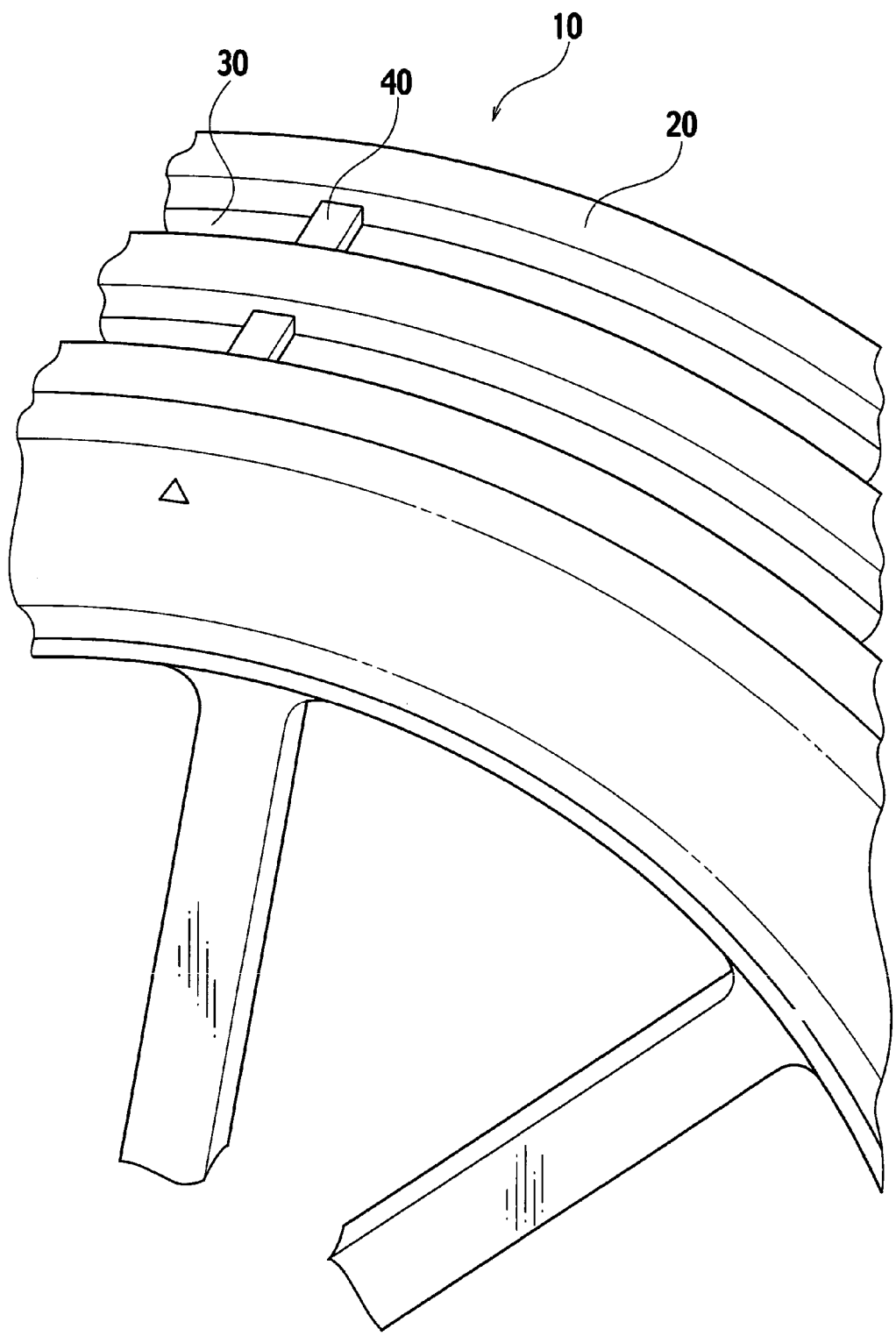
FIG. 1 is a perspective diagram of a pneumatic tire according to an embodiment.
Figure 2:
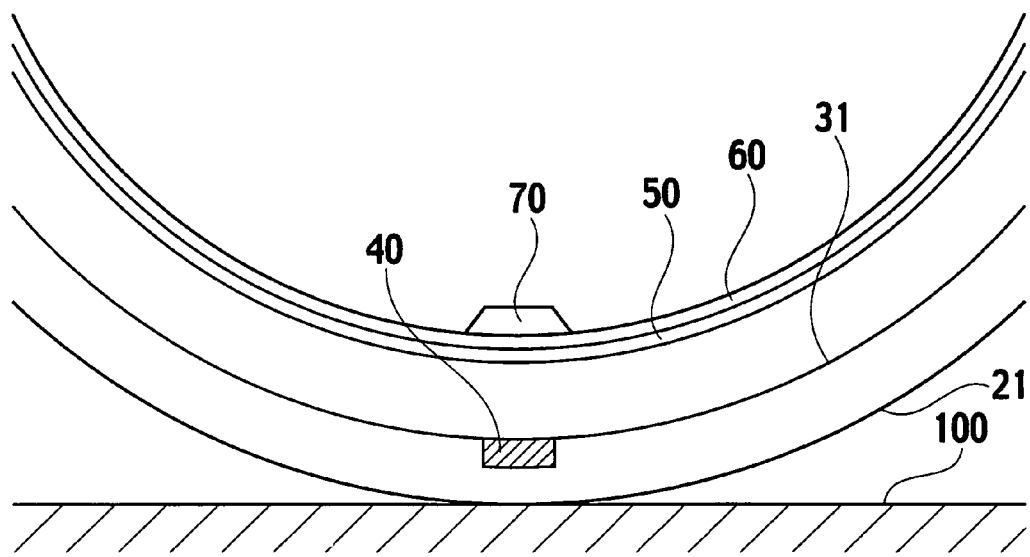
FIGS. 2(a) and 2(b) are sectional diagrams cut along a tire rolling shaft of the pneumatic tire according to the embodiment.
Figure 2:
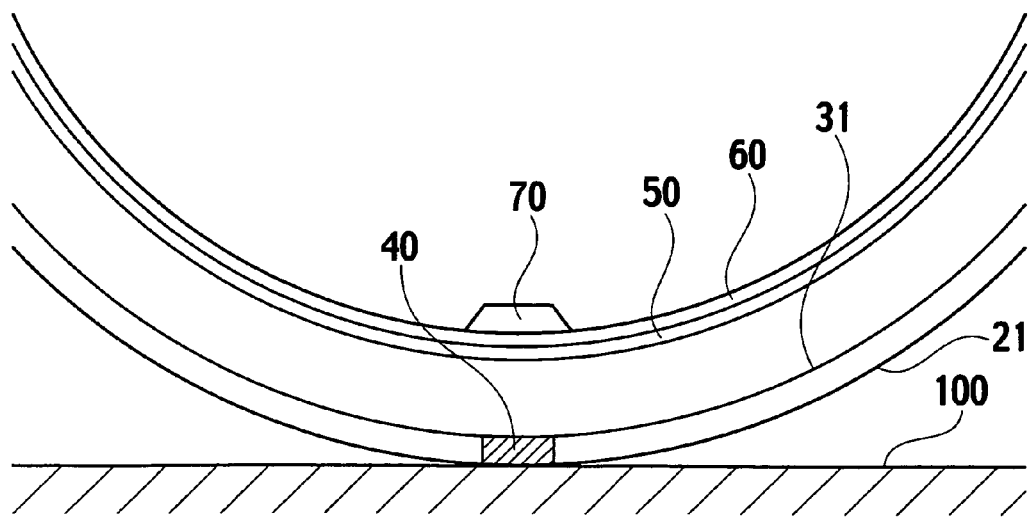

As shown in FIG. 1, a tread pattern constituted of a convex section 20 and a groove section 30 is formed in a tread section surface of a pneumatic tire 10. Wear bars 40 are arranged at certain intervals in this groove section 30.

The wear bar 40 indicates a legally stipulated lowest line of a remaining groove after wear having a height of 1.6 mm from a bottom of the groove section. In a side section of the tire, an arrow (triangle mark of FIG. 1) indicating a position of the wear bar 40 is displayed, and such arrows and wear bars 40 are normally arranged in six places of a tire circumference.

In the pneumatic tire 10 of the embodiment, as shown in FIG. 2(a), a convex surface 21 is brought into contact with a road surface 100 to roll. The wear bar 40 is arranged in a groove surface 31, and a carcass 50 which functions as a reinforcement member to hold pressure of air filling the tire, an inner liner 60 which is a rubber layer of a tire inside, and the like are arranged in the tire diameter inside of a tread section. Other parts of a structure are similar to those conventionally known, and there are no specific qualifications.

In the tire diameter inside of the wear bar 40 (surface of the inner liner 60 in the drawing), an acceleration sensor 70 (a detection unit) is arranged to detect acceleration applied to the wear bar 40 disposed in the groove of the tread section of the pneumatic tire 10.

The acceleration sensor 70 detects vibration or displacement of the wear bar 40, and acceleration applied to the wear bar 40. For example, for the acceleration sensor 70, a piezoelectric acceleration sensor, a resistive (piezo-resistive) acceleration sensor, or the like using piezoelectric ceramics is used. The piezoelectric acceleration sensor detects only a change of acceleration without holding steady rotation, while the resistive acceleration sensor holds steady acceleration so that it can estimate a rolling speed and detect the steady acceleration and a peak value of acceleration even when the speed is changed.

When the tire is worn, as shown in FIG. 2(b), the wear bar 40 is brought into contact with the road surface 100. At this time, the acceleration sensor 70 detects a large force of gravity (acceleration) as compared with a state of FIG. 2(a).

This acceleration is acceleration of a vertical direction.

Figure 3:
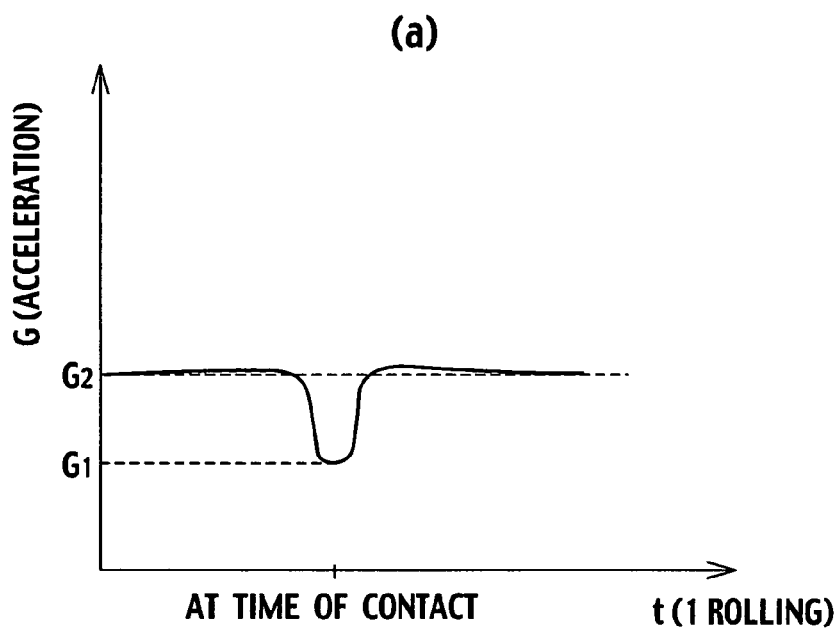
FIGS. 3(a) and 3(b) are diagrams showing examples of detection signals of an acceleration sensor according to the embodiment.
Figure 3:
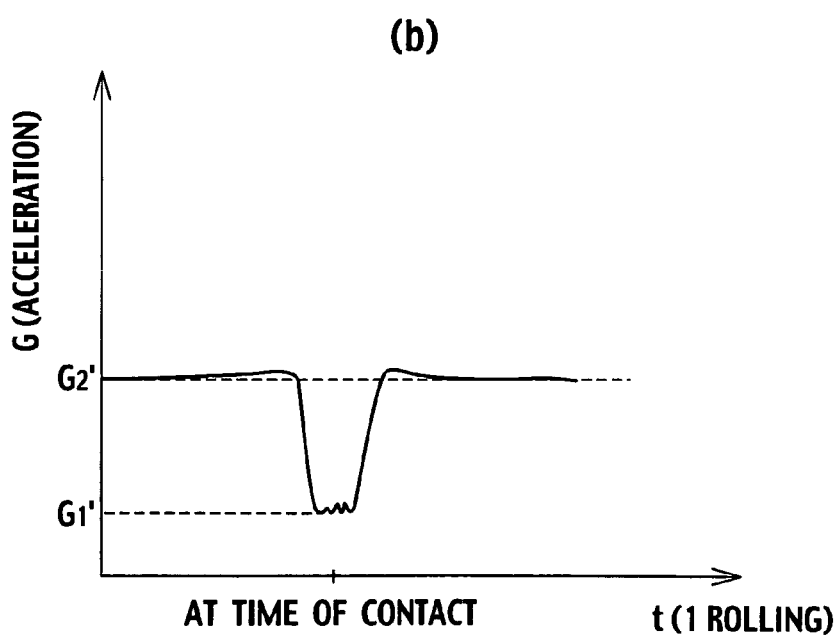

FIGS. 3(a) and 3(b) show forces of gravity (acceleration) detected by the acceleration sensor 70: FIG. 3(a) showing a new product state, and FIG. 3(b) showing a wear advanced state.

G1 in FIG. 3(a) is acceleration while a tire tread surface near the wear bar 40 is in contact with the ground when the tire is new, and G2 is acceleration while the tire tread surface near the wear bar 40 is not in contact with the ground when the tire is new. G1' in FIG. 3(b) is acceleration while the tire tread surface near the wear bar 40 is in contact with the ground, and G2' is acceleration while the tire tread surface near the wear bar 40 is not in contact with the ground.

During one rolling of the tire, the acceleration sensor 40 detects the G1 and the G2 or the G1' and G2'. A difference between G1 and G2 is small when the tire is new. However, as wear advances, larger acceleration is applied to increase the difference at the time of contact.

G2 and G2' are average values of acceleration at time other than at the time of contact. However, these are in no way limitative. Acceleration of one point other than the time of contact may be employed.

A method of judging that the tire has been worn will be described below.

In the description, the detection unit is the acceleration sensor 70 for detecting the acceleration applied to the wear bar 40. However, this is in no way limitative. The detection unit may be various sensors for detecting physical amounts equivalent to contact of the wear bar 40 with the road surface 100.

(Tire Wear Detection System)

Figure 4:
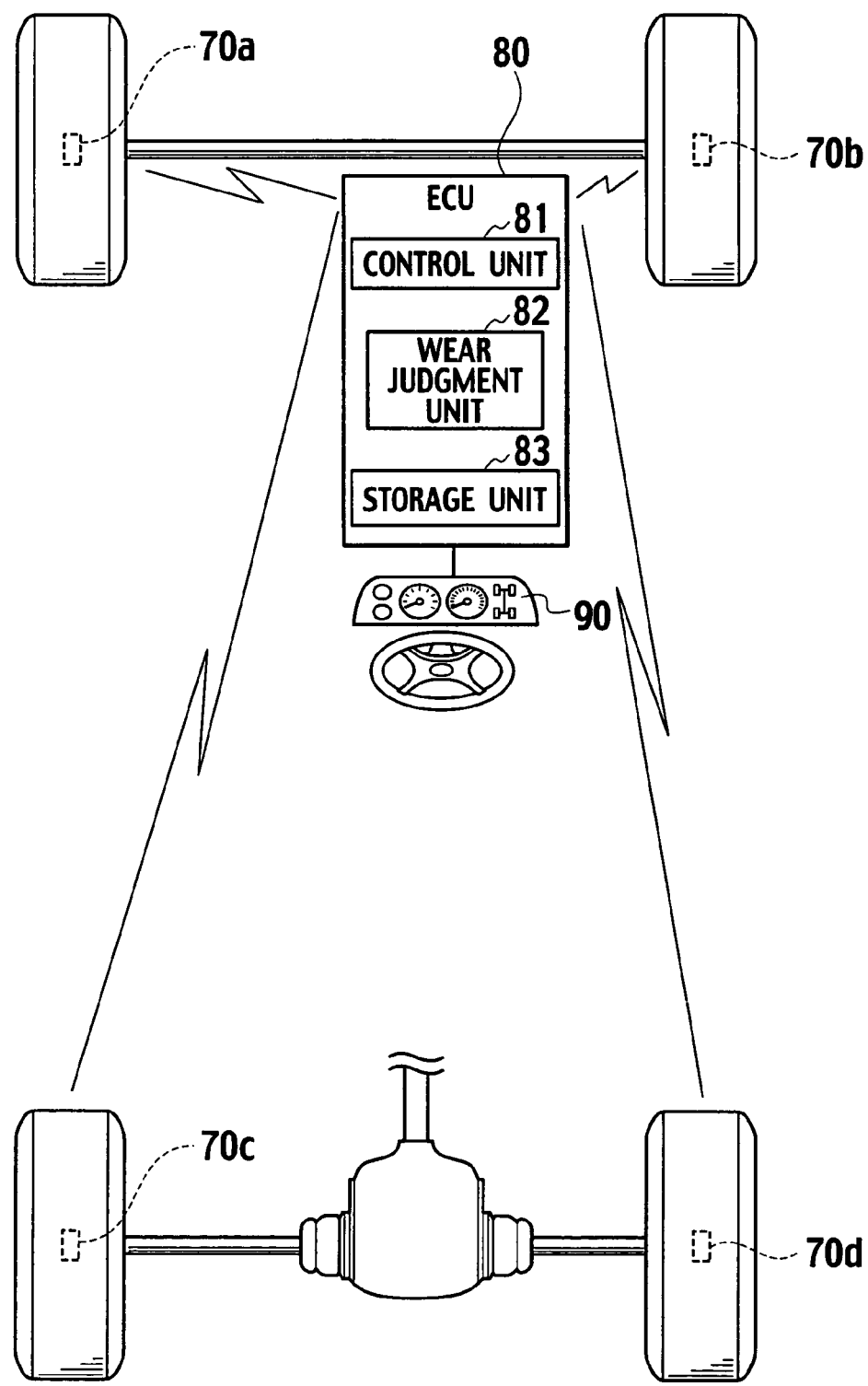
FIG. 4 is an explanatory diagram of a tire wear detection system according to an embodiment.

As shown in FIG. 4, the tire wear detection system of the embodiment is mounted in one automobile, and includes acceleration sensors (detection unis) 70a, 70b, 70c and 70d, an ECU 80, and a meter display unit 90.

The acceleration sensors 70a, 70b, 70c, and 70d detect acceleration applied to the wear bar 40 arranged in the groove of the tread section of the pneumatic tire 10, and are arranged in each tire of the automobile. In FIG. 4, one acceleration sensor is disposed per tire. Needless to say, however, a plurality of acceleration sensors may be arranged per tire. The acceleration sensors 70a, 70b, 70c and 70d output signals containing detected values to the ECU 80.

The ECU (Electronic Control Unit or Engine Control Unit) 80 includes a control unit 81, a wear judgment unit 82 (a wear judgment unit), and a storage unit 83 (a storage unit).

The wear judgment unit 82 judges that the tire has been worn based on a side of acceleration detected by the acceleration sensors 70a, 70b, 70c and 70d as means for detecting physical amounts.

Specifically, the wear judgment unit 82 receives signals output from the acceleration sensors 701, 70b, 70c and 70d. Then, the wear judgment unit 82 judges that the tire has been worn when predetermined acceleration is detected by the acceleration sensor 70.

In this case, if a wheel speed is detected by a wheel sensor (not shown) or the like, time of one tire rolling can be determined to facilitate determination of an acceleration sensor output value. Specifically, values of G2 and G2' below can be detected more easily.

When reference acceleration which becomes a reference is stored in the storage unit 83 below, and a difference between this reference acceleration and acceleration detected by the acceleration sensors 70a, 70b, 70c and 70d is equal to or higher than a certain value, the wear judgment unit 82 may judge that the tire has been worn.

The reference acceleration may be acceleration when the tire is new, or an average of acceleration detected by the acceleration sensors 70a, 70b, 70c and 70d within a predetermined time.

Presuming that K is a predetermined value larger than 1, the wear judgment unit 82 judges that the tire has been worn when acceleration detected by the acceleration sensors 70a, 70b, 70c and 70d satisfies the following equation (1):

$$G1'/G2' \geqq kG1/G2 \qquad (1)$$

The storage unit 83 is a storage medium for storing a program for executing the wear judgment unit 82, the reference acceleration, the equation (1), a pre-selected numerical value such as K, or the like. For example, a RAM or the like can be used for the storage medium. According to such a storage medium, the program or the like can be easily saved, transported, or sold.

The control unit 81 controls each unit of the automobile. For example, it decides a fuel injection amount or injection time of an engine based on information from each sensor (gauge).

The car body ECU 80 can use speed information by a car speed sensor.

The output signals from the acceleration sensors 70a, 70b, 70c and 70d to the ECU 90 may be transmitted by wire or by radio using a wireless LAN.

The meter display unit 90 reports a result of analysis of the ECU 80 by displaying it to be visually recognized. Accordingly, the driver or the like can easily and instantaneously recognize the tire wear.

The meter display unit 90 displays a speed meter and a remaining gasoline amount, and also displays detection of wear by the ECU 80. In FIG. 4, a position of the tire where the wear is detected is lit.

A place of displaying the detection of the wear is not limited to the meter display unit 90. A different display unit may be provided. In place of displaying, the detection of the wear may be reported by sound such as sounding of an alarm when the wear is detected.

(Function and Effect)

According to the pneumatic tire 10 and the tire wear detection system of the embodiment, as the tire wear detection system includes the acceleration sensor 70 for detecting the wear bar 40 arranged in the groove of the tread section of the pneumatic tire 10, and the wear judgment unit 82 for judging that the tire has been worn based on the acceleration detected by the acceleration sensor 70, it is possible to carry out highly reliable wear detection by detecting acceleration applied to the slip sensor 40. As the tire surface is not processed, the tire or the road surface is not damaged, and the appearance is not changed from that of the conventional tire.

As the wear bar 40 arranged in the tire is normally used, no new processing is necessary in the tread section.

In place of the acceleration sensor 70 for detecting acceleration, a sensor for detecting a physical amount may be used. In this case, it is possible to carry out highly reliable wear detection by detecting a physical amount applied to the wear bar 40 via the sensor. As no processing is executed for the tire surface, the tire or the road surface is not damaged, and the appearance is not changed from that of the conventional tire.

The pneumatic tire 10 further includes the storage unit 83 for storing the reference acceleration which becomes a reference, and the wear judgment unit 82 judges that the tire has been worn when a difference between the reference acceleration and the acceleration detected by the acceleration sensor 70 is equal to or higher than a certain value. Thus, it is possible to carry out highly reliable wear detection.

As the reference acceleration is acceleration when the tire is new, measurement is easy.

As the reference acceleration is an average of acceleration detected by the acceleration sensor 70 within a predetermined time, it is possible to carry out more highly reliable wear detection.

The wear judgment unit 82 judges that the tire has been worn when the acceleration detected by the acceleration sensor 70 satisfies the following equation (1):

$$G1'/G2' \geqq kG1/G2 \quad (1)$$

Thus, it is possible to carry out highly reliable wear detection.

As the acceleration is acceleration of a vertical direction, measurement is easy.

As the acceleration sensor 70 is arranged in the tire diameter inside of the wear bar 40, it is possible to detect acceleration applied to the conventionally arranged wear bar 40.

As the acceleration sensor 70 is arranged in the surface of the inner liner 60 of the pneumatic tire 10, the acceleration sensor 70 can be installed after a conventional manufacturing process. Thus, it is possible to prevent a complex manufacturing process.

According to the pneumatic tire 10 and the tire wear detection system of the embodiment, as the pneumatic tire 10 includes the acceleration sensor 70 for detecting acceleration applied to the wear bar 40 arranged in the groove of the tread section of the pneumatic tire 10, it is possible to carry out highly reliable wear detection by detecting the acceleration applied to the wear bar 40.

The pneumatic tire 10 may use a sensor for detecting a physical amount in place of the acceleration sensor 70 for detecting acceleration. In this case, it is possible to carry out highly reliable wear detection by detecting a physical amount applied to the wear bar 40 via this sensor.

INDUSTRIAL APPLICABILITY

As described above, the pneumatic tire of the present invention can be suitably used as vehicle tire since the tire wear can be detected without damaging the tire or the road surface.

The invention claimed is:

1. A tire wear detection system comprising:
a detection unit which detects acceleration applied to a wear bar arranged in a groove of a tread section of a pneumatic tire; and
a wear judgment unit which judges that a tire has been worn based on the acceleration detected by the detection unit,
wherein the detection unit is arranged in a tire diameter inside of the wear bar, and
wherein the wear judgment unit judges that the tire has been worn when the acceleration detected by the detection unit satisfies the following equation:

$$G1'/G2' \geqq kG1/G2$$

where G1 is acceleration while a tire tread surface near the wear bar is in contact with the ground when the tire is new, G2 is acceleration while the tire tread surface near the wear bar is not in contact with the ground when the tire is new, G1' is acceleration while the tire tread surface near the wear bar is in contact with the ground, G2' is acceleration while the tire tread surface near the wear bar is not in contact with the ground, and K is a predetermined value larger than 1.

2. The tire wear detection system according to claim 1, further comprising a storage unit for storing reference acceleration which becomes a reference in the pneumatic tire,
wherein the wear judgment unit also judges that the tire has been worn when a difference between the reference acceleration and the acceleration detected by the detection unit is equal to or higher than a predetermined value.

3. The tire detection system according to claim 2, wherein the reference acceleration is acceleration when the tire is new.

4. The tire wear detection system according to claim 2, wherein the reference acceleration is an average of acceleration detected by the detection unit within a predetermined time.

5. The tire wear detection system according to claim 1, wherein the acceleration is acceleration of a vertical direction.

6. The tire wear detection system according to claim 1, wherein the detection unit is arranged in a surface of an inner liner of the pneumatic tire.

7. The tire wear detection system according to claim 1, wherein the detection unit comprises a piezoelectric acceleration sensor or a piezo-resistive acceleration sensor.

* * * * *